United States Patent [19]
Munden

[11] 4,128,508
[45] Dec. 5, 1978

[54] COLOR CHANGE PERFUME SYSTEMS

[75] Inventor: David R. Munden, Hythe, England

[73] Assignee: International Octrooimaatschappij "Octropa" BV, Rotterdam, Netherlands

[21] Appl. No.: 808,737

[22] Filed: Jun. 22, 1977

[30] Foreign Application Priority Data

Jul. 2, 1976 [GB] United Kingdom ............... 27683/76

[51] Int. Cl.$^2$ ............................................... C11B 9/00
[52] U.S. Cl. ....................................... 252/522; 424/76
[58] Field of Search ........................... 252/522; 424/76

[56] References Cited

U.S. PATENT DOCUMENTS

| | | | |
|---|---|---|---|
| 2,084,465 | 6/1937 | Stoughton | 252/522 |
| 4,011,311 | 3/1977 | Noomen et al. | 424/DIG. 5 |
| 4,020,156 | 4/1977 | Murray et al. | 424/76 |

FOREIGN PATENT DOCUMENTS

| | | | |
|---|---|---|---|
| 5007137 | 1969 | Japan | 252/522 |

*Primary Examiner*—Veronica O'Keefe
*Attorney, Agent, or Firm*—Barry Kramer

[57] ABSTRACT

This invention provides a color change perfume system in which color is caused to change when the perfume in the system is effectively exhausted to the atmosphere. The invention also provides air fresheners and the like consisting of a porous carrier impregnated with the perfumed color change system.

16 Claims, No Drawings

COLOR CHANGE PERFUME SYSTEMS

DETAILED DISCLOSURE

This invention relates to colour change systems, more particularly to colour change perfume systems.

Compositions containing systems involving the use of pH indicators, which are pH sensitive dyes, together with mineral acids or alkalis which compositions, on dilution, change colour due to change of pH, have been proposed but, generally, such systems have been limited to use in applications in which the composition can be diluted with water to actuate the colour change mechanism.

It has now been found that colour change systems can be extended to volatile compositions such as perfume sources and air fresheners.

Hitherto, when an air freshening device has become exhausted, there has been no visual indication that it is no longer effective and, using the system as provided by this invention, this particular problem can readily be overcome.

Accordingly, the present invention provides a colour change perfume system comprising a reactive component in the system which component changes in contact with the atmosphere, an indicator adapted to change colour in response to changes in the reactive component and a perfume chosen to pass into the atmosphere at a selected rate, the reactive component and perfume being selected to cause the indicator to change colour when the perfume is effectively exhausted.

In one form of the invention the indicator is a standard pH indicator and the reactive component is a suitable volatile acid or base. In this form of the invention the volatility of the acid or base is selected to be similar to the volatility of the perfume composition, so that when the acid or base has volatilised and the pH indicator changed colour, so informing the user that the effective life of the perfume has, or is about to cease.

Suitable indicators for use in the system as provided by this invention are described in Kirk-Othmer, 2nd Edn., Vol. 11, pages 548 to 560. It will be seen here that indicators can be used for acid base reactions, oxidation reduction reactions and as coloured compounds which can be caused to change colour. Clearly, the invention can be applied with appropriate reagents to any of these systems. Particularly convenient indicators for use in the systems according to this invention include: bromocresol green, bromocresol purple and bromothymol blue.

In addition to the colour change indicator, the system can also comprise coloured compounds which can give a pleasing colour to the system and modify the actual colour change. For example, if the colour change is from blue to colourless, if a yellow compound is mixed into the system, the colour change will become green to yellow and, in certain applications, this is a more pleasing effect.

Volatile bases suitable for use in this invention in its various forms include: 2-amino-2-methyl-1-propanol, 2-dimethyl-amino-2-methyl-1-propanol, monoethylamine, diethylamine, morpholine, di-n-butylamine, diisopropylamine and ammonium hydroxide.

Acids suitable for use in the invention include: hydrochloric acid, acetic acid, malonic acid, lactic acid, succinic acid and benzoic acid.

It will be understood that both the acid and base will affect the odour from the system and, hence, must be chosen with care.

In a preferred form of the invention, the reactive component comprises an alkali, such as sodium hydroxide, which reacts chemically with carbon dioxide which is absorbed from the air. In this form of the invention, no odour problem arises from the reactive component.

The system can be made up largely of the essential components, or, for certain applications, a cheaper system may be provided comprising a significant proportion of water.

In the water based system, the perfume and indicator are conveniently solubilised by the inclusion of a suitable solvent selected to enhance the solubility of the perfume and, if necessary, the indicator, in water.

In addition, a water based system may comprise a suitable surfactant or emulsifier designed to disperse or solubilise the non-water-soluble components of the system into the water phase. Suitable surfactants include: salts of alkyl or aryl sulphosuccinates, alkyl phenol ethoxylates, alcohol ethoxylates, amine ethoxylates, ethoxylated fatty acid esters, ethoxylated esters of fatty acids and polyols. Other suitable surfactants will readily be found by reference to standard textbooks such as, Schwartz, Perry & Berch.

The colour change perfume systems provided by this invention can be absorbed into absorbent bases such as paper, cellulose or unglazed ceramics and, in this form, are valuable as colour change air fresheners.

The absorbent substrate used greatly affects the rate of colour change and the related exhaustion of perfume from the system. Likewise, the environment in which the colour change system is used affects the rate of exhaustion of perfume from the system and the related colour change. For example, in a draughty room in which the air is changed rapidly, the system will become exhausted very much more rapidly than in a smaller room with closed doors and windows. In addition, solvents or solubilisers used and the humidity will have a significant effect on the rate of change of the water based systems.

In a preferred form of the colour change system provided by this invention, at least 50% by weight of the system consists of water and comprises an amount of an emulsifying agent sufficient to emulsify the perfume into the water phase of the system.

The following examples further illustrate the invention. All parts are expressed by weight. The words "Carbitol" and "Triton" and "Cropol" are Trade Marks. Triton X100 is an octyl phenol ethoxylate.

EXAMPLE 1

A balanced colour change perfume discharge system having a blue to yellow colour change was prepared from:

| Components | % w/w |
|---|---|
| Deionised water | to 100.00 |
| Perfume (fruity pine type - details given below | 10.00 |
| Alcohol | 20.00 |
| Carbitol | 20.00 |
| Formaldehyde (40% aqueous) | 00.20 |
| Triton X100 (surfactant) | 10.00 |
| Bromothymol blue | 00.10 |
| Morpholine (amine) | 01.00 |

The alcohols are used to solubilise the perfume in the aqueous components and modify its evaporation rate, and the morpholine is the reactive component which volatilises into the atmosphere changing the pH of the system.

| Fruity Pine Perfume Components | % w/w |
|---|---|
| Benzyl acetate | 08.00 |
| Bornyl acetate | 69.00 |
| Citronellol standard | 04.00 |
| Dimethyl benzyl carbinol acetate | 00.50 |
| Linalol | 04.00 |
| Methyl ionone | 06.00 |
| Phenyl ethyl acetate | 03.50 |
| Terpineol | 04.00 |
| Undecalactone 10% | 01.00 |

Using this level of morpholine, the colour took four days at an average temperature of about 27° C. to change completely and the perfume had lost its effectiveness over the same period when carried on a porous ceramic disc.

EXAMPLE 2

A balanced colour change perfume discharge system having a blue to red to yellow colour change was prepared from:

| Components | % w/w |
|---|---|
| Deionised water | to 100.00 |
| Perfume (Rose type - details given below) | 10.00 |
| Alcohol | 20.00 |
| Carbitol | 20.00 |
| Formaldehyde (40% aqueous) | 00.20 |
| Triton X100 (surfactant) | 10.00 |
| Ethyl orange | 00.05 |
| Hydrochloric acid - concentrated | 02.50 |
| Rose Perfume Components | % w/w |
| Citronellol | 10.00 |
| Hydroxycitronellal | 10.00 |
| Phenyl ethyl alcohol | 23.00 |
| Tetra hydro geraniol | 07.00 |
| Methyl ionone | 08.00 |
| Phenyl ethyl acetate | 07.00 |
| Cyclamen aldehyde | 05.00 |
| Amyl cinnamic aldehyde | 10.00 |
| Linalol | 10.00 |
| Eugenol | 01.00 |
| Citronellyl formate | 05.00 |
| Anisic aldehyde | 03.00 |
| Rose oxide 10% | 02.00 |
| Phenyl acetic aldehyde dimethyl acetal | 02.00 |

In this Example the hydrochloric acid is the reactive component and when it evaporates from the system the pH rises and colour change occurs.

With this level of hydrochloric the colour took six to 7 days at about 27° C. to change completely and the perfume was exhausted over a similar period on a disc as used in Example 1.

It will be appreciated that by varying the concentration of the acid or base the time taken for the colour change to occur can be varied and, if such changes are made, the perfume formulation or concentration will need to be modified if a balanced exhaustion is to occur.

EXAMPLE 3

A green to yellow colour change air freshener system was prepared from the following components. In this Example sodium hydroxide is the reactive component and is changed by contact with $CO_2$ from the atmosphere to cause a drop in pH in the system.

| Components | % w/w |
|---|---|
| Perfume (Pine needle green sweet type - details given below) | 75.00 |
| Carbitol | to 100.00 |
| Bromothymol blue | 0.025 |
| Oil soluble dye (FD&C yellow No. 11) (1971 Colour Index 47000) | 0.10 |
| Sodium hydroxide (as 20% solution) | 0.10 |

| Pine Needle Green Sweet Perfume Components | % w/w |
|---|---|
| Aldehyde $C_9$ 10% | 0.50 |
| Aldehyde $C_{10}$ 10% | 1.00 |
| Methyl nonyl aldehyde 10% | 3.00 |
| Anisic aldehyde | 5.00 |
| Bergamot synthetic | 8.00 |
| Bornyl acetate | 50.00 |
| Citronellol | 2.00 |
| Coumarin | 5.00 |
| Geranyl acetate | 3.00 |
| Lavandin | 2.00 |
| Lixetone | 2.50 |
| Musk ambrette | 2.00 |
| p-Tertiary butyl cyclohexyl acetate | 3.00 |
| Terpinoline | 5.00 |
| Versalide | 2.00 |
| Galbanum | 0.50 |
| Orange oil sweet | 0.80 |
| Rosemary | 2.00 |
| Linalyl acetate | 1.70 |
| Elemi gum | 1.00 |

This air freshener system applied to a compressed cellulose board 2mm thick had an effective life of approximately 5 weeks at an average temperature of 22° C.

EXAMPLE 4

A green to yellow pine colour change air freshener system was prepared from the following components:

| Components | % w/w |
|---|---|
| Deionised water | to 100.00 |
| Carbitol | 10.00 |
| Triton X100 (surfactant) | 10.00 |
| Perfume (as in Example 3) | 10.00 |
| Sodium hydroxide | 0.20 |
| Bromoothymol blue | 0.10 |
| Water soluble dye (FD&C yellow No. 5) (1971 Colour Index 19140) | 0.05 |
| Formaldehyde | 0.02 |

This air freshener system was carried on a compressed cellulose board 2mm thick. The colour changed and the perfume was effectively exhausted after 2 weeks' exposure in a living room.

EXAMPLE 5

A red to yellow colour change air freshener system was prepared from the following components:

| Components | % w/w |
|---|---|
| Perfume (as in Example 2 | 74.00 |
| Water | 1.00 |
| Dipropylene glycol | to 100.00 |
| Ethyl orange | 0.075 |
| Hydrochloric acid (concentrated) | 1.00 |

This system gave a colour change and perfume exhaustion in 3 to 4 weeks when applied to compressed cellulose approximately 2mm thick.

EXAMPLE 6

This Example illustrates an emulsion system which is entirely satisfactory if a clear system is not required. This Example also illustrates the use of a coloured dye to modify the colour change which is given by the indicator.

The components of the system are as follows:

| Components | % w/w |
|---|---|
| Bromothymol blue | 0.05 |
| Cropol 60 (Sodium dioctyl sulpho-succinate) | 1.00 |
| Perfume (as in Example 3) | 10.00 |
| Formaldehyde | 0.20 |
| Deionised water | to 100.00 |
| Sodium hydroxide (as 20% solution) | 0.20 |
| Water soluble dye (FD&C yellow No. 5) (1971 Colour Index 19140) | 0.05 |

This emulsion system requires shaking before use to ensure uniformity of the composition and, when applied to a 2mm thick compressed cellulose base, a green to yellow colour change and perfume exhaustion occur in about 4 weeks in normal household conditions.

What is claimed is:

1. A colour change perfume system comprising (1) a volatile acid or base, (2) a perfume adapted to pass into the atmosphere at a selected rate, and (3) a pH indicator, the volatile acid or base being selected and being present in such amount as to volatize at about the same rate as the perfume, thereby causing the pH indicator to change colour when the perfume is effectively exhausted.

2. A system as claimed in claim 1 in which component (1) is a volatile acid.

3. A system as claimed in claim 2 in which the volatile acid is acetic acid.

4. A system as claimed in claim 2 in which the volatile acid is hydrochloric acid.

5. A system as claimed in claim 1 in which component (1) is a volatile base.

6. A system as claimed in claim 5 in which the volatile base is an amine.

7. A system as claimed in claim 1 in which the system is clear and aqueous and comprises a surfactant and a solvent selected to enhance the solubility of the perfume in water.

8. A system as claimed in claim 7 in which the solvent is a mono- or polyhydric alcohol.

9. A system as claimed in claim 1 in which at least 50% by weight of the system consists of water and the system comprises an amount of an emulsifying agent sufficient to emulsify the perfume into the water phase of the system.

10. A colour change perfume system as claimed in claim 1 in combination with an impregnatable porous carrier.

11. A colour change perfume system comprising (1) an alkali which reacts with carbon dioxide absorbed from the air, (2) a perfume adapted to pass into the atmosphere at a selected rate, and (3) a pH indicator, the alkali being selected and being present in such amount as to react with carbon dioxide at about the same rate as the perfume passes into the atmosphere, thereby causing the pH indicator to change colour when the perfume is effectively exhausted.

12. A system as claimed in claim 11 in which the alkali is sodium hydroxide.

13. A system as claimed 11 in which the system is clear and aqueous and comprises a surfactant and a solvent selected to enhance the solubility of the perfume in water.

14. A system as claimed in claim 13 in which the solvent is a mono- or polyhydric alcohol.

15. A system as claimed in claim 11 in which at least 50% by weight of the system consists of water and the system comprises an amount of an emulsifying agent sufficient to emulsify the perfume into the water phase of the system.

16. A colour change perfume system as claimed in claim 11 in combination with an impregnatable porous carrier.

* * * * *

UNITED STATES PATENT OFFICE

CERTIFICATE OF CORRECTION

Patent No. 4,128,508 Dated December 5, 1978

Inventor(s) David R. Munden

It is certified that error appears in the above-identified patent and that said Letters Patent are hereby corrected as shown below:

IN THE CLAIMS:

In Claim 13, line 1, after "Claimed" and before "11" should read --in Claim--.

Signed and Sealed this

*Twentieth* Day of *March 1979*

[SEAL]

*Attest:*

RUTH C. MASON
*Attesting Officer*

DONALD W. BANNER
*Commissioner of Patents and Trademarks*